United States Patent [19]

Stookey

[11] Patent Number: 6,080,419
[45] Date of Patent: Jun. 27, 2000

[54] PREVENTION OF DENTAL CALCULUS FORMATION WITH POLYCARBOXYLIC ACIDS

[75] Inventor: George K. Stookey, Noblesville, Ind.

[73] Assignee: Advanced Research and Technology Institute, Inc., Indianapolis, Ind.

[21] Appl. No.: 09/083,510

[22] Filed: May 22, 1998

[51] Int. Cl.⁷ .............................. A61K 7/16; A61K 7/24; A63K 1/16; A63K 1/20; A23L 1/30

[52] U.S. Cl. .............................. 424/442; 424/49; 424/55; 426/805; 426/807; 426/808; 426/810

[58] Field of Search ................................ 424/49–58, 439, 424/442; 426/805, 806, 807, 868, 810

[56] References Cited

U.S. PATENT DOCUMENTS

| | | | |
|---|---|---|---|
| 3,598,606 | 8/1971 | Spinelli | 99/7 |
| 3,679,429 | 7/1972 | Mohrmon et al. | 99/2 |
| 3,930,031 | 12/1975 | Kealy | 426/89 |
| 4,011,346 | 3/1977 | Ernst | 426/104 |
| 4,027,043 | 5/1977 | Schroeder et al. | 426/69 |
| 4,127,678 | 11/1978 | Burkwall, Jr. | 426/250 |
| 4,143,125 | 3/1979 | Dyroff et al. | 424/49 |
| 4,205,093 | 5/1980 | Blake | 426/333 |
| 4,215,149 | 7/1980 | Majlinger | 426/292 |
| 4,371,558 | 2/1983 | Siregar et al. | 426/332 |
| 4,400,372 | 8/1983 | Muhler et al. | 424/48 |
| 4,444,796 | 4/1984 | Ueno et al. | 426/335 |
| 4,904,494 | 2/1990 | Spanier | 426/646 |
| 4,904,495 | 2/1990 | Spanier | 426/646 |
| 4,938,976 | 7/1990 | Shemer | 426/104 |
| 5,000,972 | 3/1991 | Nafisi-Movaghar | 426/333 |
| 5,186,964 | 2/1993 | Gierhart et al. | 426/74 |
| 5,188,861 | 2/1993 | Mazin et al. | 426/640 |
| 5,215,740 | 6/1993 | Domke et al. | 424/52 |
| 5,296,217 | 3/1994 | Stookey | 424/57 |
| 5,401,522 | 3/1995 | Reeg | 426/549 |
| 5,532,010 | 7/1996 | Spanier et al. | 426/94 |
| 5,554,358 | 9/1996 | Williams et al. | 424/49 |
| 5,618,518 | 4/1997 | Stookey | 424/57 |
| 5,690,988 | 11/1997 | Lin et al. | 426/635 |
| 5,705,207 | 1/1998 | Cook et al. | 426/89 |

FOREIGN PATENT DOCUMENTS

| | | | |
|---|---|---|---|
| 1 071 922 | 2/1980 | Canada. | |
| 2403795 | 12/1977 | France | A61K 7/16 |
| 56-160980 | 12/1981 | Japan. | |
| 57-016682 | 2/1982 | Japan. | |
| 58-198254 | 11/1983 | Japan. | |
| 1 179 343 | 1/1970 | United Kingdom. | |
| 1 230 514 | 5/1971 | United Kingdom. | |
| 1 419 902 | 12/1975 | United Kingdom. | |
| 1 474 629 | 5/1977 | United Kingdom. | |
| 93/25087 | 12/1993 | WIPO. | |

OTHER PUBLICATIONS

Briner et al Calcified Tissue Research 11(1):10–22 "In Vitro and In Vivo Evaluation of Anti–Calculus Agents", Jan. 1973.

*Primary Examiner*—Shep K. Rose
*Attorney, Agent, or Firm*—Schwegman, Lundberg, Woessner & Kluth, P.A.

[57] ABSTRACT

The present invention provides a method to prevent, inhibit, or reduce dental calculus deposits or formation on the teeth of a dental calculus forming animal comprising exposing the teeth to a food product comprising an acidulent amount of phosphoric acid, wherein said food product further comprises an amount of a polycarboxylic acid sequestering agent effective to prevent, inhibit, or reduce dental calculus deposits or formation. The present invention further provides the food products and the method of preparing the food products of said method.

14 Claims, No Drawings

PREVENTION OF DENTAL CALCULUS FORMATION WITH POLYCARBOXYLIC ACIDS

BACKGROUND OF THE INVENTION

Dental calculus, or tartar, is a recurring calcified deposit on the surfaces of the teeth of many mammals, including humans, and domesticated dogs and cats. It is generally recognized that dental calculus develops in a sequential process that involves the accumulation of dental plaque and the subsequent calcification of the plaque by saliva, which contains very high concentrations of calcium and phosphate. Although calculus, per se, is not directly responsible for the development of oral diseases, it is considered to be a secondary, or contributing factor in the development of periodontal disease because: (1) its presence on the teeth serves as a local irritant to the adjacent soft tissues, eliciting an inflammatory response (and soft tissue inflammation is the initial phase of periodontal disease); (2) it interferes with the normal cleansing of the tooth surfaces, which occurs during the mastication of food or through the performance of conventional oral hygiene procedures, such as tooth brushing and flossing; and (3) by virtue of its porosity, it harbors bacterial toxins, which exacerbate periodontal disease formation.

Consequences of periodontal disease can include systemic infection, alveolar bone recision, tooth decay and loss, and adverse mouth and breath odors. Once formed, calculus deposits can only be removed through dental prophylaxis or other mechanical procedures. Thus, the prevention of dental calculus is of importance not only for cosmetic reasons, but also because of dental calculus' secondary role in the development of periodontal disease, and the resultant systemic infections, alveolar bone recision, tooth loss and adverse mouth and breath odors.

Currently, dental calculus formation may be prevented in three ways. First, dental calculus formation can be prevented by meticulous, daily removal of dental plaque prior to its calcification. Second, dental calculus formation can be prevented by the daily application of crystal growth inhibitors that interfere with the calcification of dental plaque by saliva. Recognized crystal growth inhibitors include various soluble pyrophosphates, sodium tripolyphosphate, soluble diphosphonates, and certain soluble zinc compounds, such as zinc chloride. These crystal growth inhibitors are used in dentifrices and mouthwashes for prevention of calculus formation in humans and animals. Soluble pyrophosphates are currently cooked or baked into the dough of commercially-prepared foods for domesticated dogs and cats in order to prevent or reduce dental calculus formation in these animals. Third, dental calculus formation may be prevented by the use of sodium hexametaphosphate. U.S. Pat. No. 5,296,217, issued on Mar. 22, 1994, and U.S. Pat. No. 5,618,518, issued on Apr. 8, 1997, disclose that sodium hexametaphosphate can prevent or reduce calculus build-up when applied as a coating to dry pet foods, pet chew products, or when mixed with moist foods. Sodium hexametaphosphate is currently incorporated into some commercially-available dry dog and cat diets, as well as snack foods, to prevent dental calculus formation.

However, many food products arc incompatible with sodium hexametaphosphate. For example, some commercially-prepared dry foods for cats and dogs are surface coated with phosphoric acid, which is used as an organoleptic and a palatant. In addition, some commercially-prepared moist foods for cats and dogs contain phosphoric acid, for the same reasons mentioned above. When sodium hexametaphosphate is applied as a final coating over a food product which has been coated with or contains phosphoric acid, the hexametaphosphate is converted to other forms of phosphate, predominantly orthophosphate. This chemical conversion destroys the ability of the hexametaphosphate to prevent calculus formation. Thus, incorporation of sodium hexametaphosphate into animal foods previously coated with or containing phosphoric acid actually negates the beneficial effects of sodium hexametaphosphate.

Therefore, a need exists for food products or methods that are useful to control or reduce calculus formation in animals, and that are suitable for, and compatible with, foods treated with or containing phosphoric acid.

SUMMARY OF THE INVENTION

The present invention provides a method to inhibit dental calculus formation on the teeth of a dental calculus forming animal by exposing the teeth of the animal to a food product containing an acidulent amount of phosphoric acid, wherein said food product further comprises an effective calculus-inhibiting amount of a polycarboxylic acid sequestering agent. Following ingestion, the sequestering agent is believed to function in situ to form soluble calcium complexes in saliva and dental plaque components so as to prevent the calcification of dental plaque. Useful polycarboxylic acid sequestering agents include organic polycarboxylic acids, such as those comprising 2–4 carboxylic acid groups. Preferred polycarboxylic acid sequestering agents include malic acid, fumaric acid and citric acid, used individually or in combination. When incorporated into or applied onto the surface of animal food products that have previously been treated with an acidulent amount of phosphoric acid, the polycarboxylic acid sequestering agents remain effective to prevent, reduce, or inhibit the formation of dental calculus on the teeth of animals. Further, when incorporated into moist or dry animal food products that contain an acidulent amount of phosphoric acid, the polycarboxylic acid sequestering agents can prevent, reduce, or inhibit the formation of dental calculus on the teeth of animals. Preferably, the polycarboxylic acid is present in an amount of about 0.05–10.0 weight-% of the food product, preferably about 0.2–3.0 weight-%, most preferably about 0.5–2.0 weight-%.

The preferred polycarboxylic acid sequestering agents are compatible with phosphoric acid, which is used as a coating in some commercially prepared food products. Phosphoric acid can be applied to or mixed into commercially prepared food products, particularly cat food products, as an acidulent, for palatability and organoleptic purposes. Another sequestering agent, sodium hexametaphosphate can be used as a coating for pet foods and pet chew products. However, sodium hexametaphosphate is not compatible with phosphoric acid. When hexametaphosphate is applied as a coating over a food product previously coated with or containing phosphoric acid, hexametaphosphate undergoes a chemical conversion that destroys its ability to prevent calculus formation. Thus, the present invention provides a marked improvement over the prior art sequestering agent, hexametaphosphate, as it is superior in terms of compatibility with conventional dietary and physiological requirements met by presently available commercially-prepared food products.

Preferably, the polycarboxylic acid sequestering agent is applied as a coating onto, or mixed with, an animal food comprising phosphoric acid. Preferably said food does not contain a hexametaphosphate salt, such as sodium hexametaphosphate, as its conversion to orthophosphate by phosphoric acid may increase calculus formation, thereby reducing the benefits of the polycarboxylic acid coating.

The preferred polycarboxylic acids discussed above, when placed separately or in combination in a liquid carrier to form a solution or a dispersion, and allowed to contact the teeth of animals at an effective dose, can also prevent, reduce, or inhibit the formation of dental calculus on the teeth of said animals. In yet another aspect of the present invention, tooth contact is achieved utilizing solutions or dispersions containing effective doses of polycarboxylic acids, such as malic acid, fumaric acid, citric acid, or a combination of these acids.

The present invention also provides a method of preparing a food product that is effective to prevent or reduce the formation of dental calculus that comprises the application onto, or incorporation in, said food product, of an effective amount of a polycarboxylic acid sequestering agent, such as malic acid, fumaric acid, citric acid or a combination thereof.

Further, the present invention provides a food product capable of preventing, reducing, or inhibiting the formation of dental calculus in animals, wherein said product comprises phosphoric acid and an effective anti-calculus amount of a polycarboxylic acid, such as malic acid, fumaric acid, citric acid, or a combination of these acids.

As used herein, the term "inhibit" includes preventing calculus formation as well as reducing calculus deposits or rate of formation or accumulation by a measurable amount.

DETAILED DESCRIPTION OF THE INVENTION

All percentages herein are by weight unless otherwise noted.

Polycarboxylic Acid Sequestering Agents

Polycarboxylic acid sequestering agents, or sequestrants, are those capable of forming soluble coordination complexes with various cations such as alkaline earth cations so as to prevent their usual precipitation from aqueous solution as insoluble deposits. The polycarboxylic acid sequestering agents utilized in this invention comprise about 3–12 carbon atoms and can include about 2–3 carboxylic acid ($CO_2H$) groups. Preferred polycarboxylic acid sequestering agents are malic acid ($HO_2CCH_2CH(OH)CO_2H$), fumaric acid ($HO_2CCH=CHCO_2H$), and citric acid ($HO_2CCH_2C(OH)(CO_2H)CH_2CO_2H$). Nontoxic or water soluble palatable salts of these acids may also be used in the present invention, such as alkali metal salts.

The use of polycarboxylic acids in the present invention is advantageous for a number of reasons. The biological, toxicological, and pharmacological safety of these polycarboxylic acids upon animal ingestion is demonstrated by their acceptance as GRAS by the U.S. Food and Drug Administration. Relatively low concentrations of polycarboxylic acids can be efficacious for prevention of dental calculus formation in animals. The efficacy of polycarboxylic acids in the prevention of dental calculus formation is markedly superior as compared to prior art crystal growth inhibitors, when both are used as described on foods also having a surface coating of phosphoric acid as a palatant. Polycarboxylic acids are compatible with commercially-prepared dry foods for cats and dogs that are surface coated with phosphoric acid, unlike hexametaphosphate. Polycarboxylic acid sequestering agents can readily be incorporated or mixed into commercially-prepared moist animal food product. Finally, the use of polycarboxylic acids as a coating for animal foods does not deleteriously alter the organoleptic and palatability characteristics of the food products.

Animals

The present invention may be utilized to treat a variety of animals. Preferable animals include mammals; humans; cats, including domesticated cats as well as exotic animals, including lions, tigers, cougars, lynx, bobcats, mountain lions, mink, ferrets; dogs, including domesticated dogs, and wolves; primates, including baboons, monkeys, and apes; bears; lemurs; and rodents.

Food Product Composition

Preferable food products for use in this invention include rations and snack foods for dogs and cats, as well as food for human ingestion, such as processed cereals and snack foods. Said food products preferably contain an amount of polycarboxylic acid, either applied onto the surface of or mixed into the food products.

The present invention provides food products referred to herein as rations and snack foods. As used herein, the term "dog ration" or "cat ration" for purposes of this invention denotes an allowance or measure of food to sustain the daily dietary and nutritional needs of an average domesticated dog or cat, respectively. Dog or cat rations may be formulated so as to be dry or moist. Dry rations typically contain a minimum of about 5–50% crude protein, a minimum of about 0.5–25% crude fat, a maximum of about 1–10% crude fiber, and a maximum of about 1–30% moisture. Moist rations typically contain a minimum of about 0.5–40% crude protein, a minimum of about 0.5–25% crude fat, a minimum of about 0.5–15% crude fiber, a maximum moisture content of about 60–95%, a maximum of about 0.1–20% ash, a minimum of about 0.001–5.0% taurine, and water in an amount sufficient for processing.

As used herein, the terms "dog snack food" and "cat snack food" are used to refer to food items which are intended to augment or supplement a ration, to remove dental plaque through the normal mastication process, or simply entertain or amuse a dog or cat, respectively. Typical snack foods contain a minimum of about 5–45% crude protein, a minimum of about 0.5–25% crude fat, a maximum of about 0.25–20% crude fiber, and a maximum of about 0.5–50% moisture. The forms of snack foods vary greatly, and may encompass shapes such as biscuits, crackers, rings, kernels, wafers, or bones.

As used herein, the term "human food" is used to refer to nutritious food products which are intended to augment or supplement the human diet, while removing dental plaque through the normal mastication process. The form of human snack foods varies greatly, and may encompass shapes such as biscuits, crackers, kernel, wafers, rings, and items commonly referred to as chips, pretzels, cookies, crackers, bars, wafers, rice cakes, puffed corn or rice products, and biscuits.

The above-described food products preferably contain components of starch or carbohydrates, animal or fish proteins, animal or fish by-products, coloring agents, flavoring agents and palatants, sources of fat, stabilizers, emulsifiers, texturizers, thickening and binding agents, leavening agents, preservatives, nutritional factors, dietary components, and vitamin supplements.

The present rations and snack foods can contain an amount of carbohydrate or starch. Useful carbohydrate or starch components include cereals and grains, including ground yellow corn, ground white corn, puffed corn, modified corn starch, corn gluten meal, rice, rice flour, crisp rice, brewers rice, rice flour, barley, ground barley, soybean, soybean meal, soy flour, oats, oat gluten, oat flour, oatmeal, tapioca, tapioca starch, wheat, wheat bran, wheat flour, bleached wheat flour, unbleached wheat flour, wheat gluten, defatted wheat germ, toasted whole wheat, malt, and whole wheat flour.

Forms of animal or fish protein may be present in the present rations and snack foods. For dogs and cats, such proteins include by-products and by-product meals, digests and bone meal, from beef, chicken, pork, veal, turkey, poultry, lamb, or fish. Preferred protein forms for use in human snack foods generally comprise animal proteins, including beef, chicken, pork, veal, turkey, poultry or lamb protein, as well as milk solids, such as sodium caseinate and whey.

Leavening agents can be present in rations and snack foods. Preferred leavening agents include sodium bicarbonate, sodium acid pyrophosphate, and monocalcium phosphate.

Coloring agents can also be included in the present rations and snack foods. Useful coloring agents include caramel coloring, yellow dyes #5 & #6, titanium dioxide, and iron oxide.

Fat is included in the present rations and snack foods. Preferable sources of fat in the present rations and snack foods include vegetable oil, canola oil, safflower oil, sunflower oil, cottonseed oil, soybean oil, peanut oil, olive oil, and butter. These oils may be present in human snack foods in the hydrogenated or partially hydrogenated form.

The present rations and snack foods can incorporate palatants and flavoring agents, to enhance the taste and flavor of the products. Preferable palatants and flavoring agents include salt, natural flavors, artificial flavors, spices, yeast, brewers dried yeast, yeast extract, fermented soy, sugars, corn sweeteners, nuts, sesame seeds and phosphoric acid.

Stabilizers, protective colloids, emulsifiers, texturizers, thickening and binding agents can also be included in the present snack foods and rations, including guar gum, locust bean gum, carrageenan, iron oxide, powdered cellulose, modified cellulose, sodium alginate, xanthan gum, and propylene glycol.

The present rations and snack foods can contain preservatives and antioxidants which inhibit biodegradation, fermentation, mold growth and infestation by other organisms, such as rodents or insects. Useful preservatives and antioxidants include ethoxyquin, propylene glycol, parabens and potassium sorbate.

Nutritional factors, dietary supplements, and vitamin supplements can also be contained in the present rations and snack foods. Preferable nutritional factors and dietary supplements include zinc sulfate, ferrous sulfate, potassium chloride, calcium carbonate, choline chloride, niacin, copper sulfate, manganese sulfate, calcium pantothenate, folic acid, potassium iodide, biotin, sodium selenite, DL methionine, ferrous sulfate, dicalcium phosphate, niacin, and copper sulfate. Preferable vitamin supplements include vitamins A, C, E, B12, D3, thiamine mononitrate and thiamine hydrochloride (vitamin B1), riboflavin supplement (Vitamin B2), pyridoxine hydrochloride (Vitamin B6), and menadione sodium bisulfite complex (source of vitamin K activity).

For dogs and cats, the present rations and snack foods may also contain compounds as palatants, such as phosphoric acid, as well as compounds having antacid and antidiarrheal utility, such as calcium carbonate, kaolin and the like.

Description of Animal Studies

The invention will be further described by reference to the following detailed examples, that were designed to evaluate measures and agents for the prevention of dental calculus formation. A group of 24 colony-bred adult female cats and 24 beagle dogs was used. The animals were continuously housed in stainless steel cages in an AAALAC-accredited facility in the Indiana University School of Dentistry. To establish the normal rate of calculus formation for each animal, a thorough dental prophylaxis (cleaning) was performed on each animal to remove all existing calculus and other exogenous deposits (plaque, pellicle, debris) from all of their teeth. The cats were then provided with a Kal Kan Whiskas® dry diet, which is a commercially-available, nutritionally balanced cat ration. Kal Kan Whiskas® dry diet contains 0.5 weight-% phosphoric acid. The cats were fed an amount of diet on the basis of body weight (about 20 g/kg body weight). This feeding was provided once daily throughout a 28-day test period.

The dogs were provided with Waltham Dry Adult Conditioning Formula® brand diet, which is a nutritionally balanced, commercially-available dog ration. Waltham Dry Adult Conditioning Formula® brand diet contains 0.25 weight-% phosphoric acid. The dogs were fed an amount of diet on the basis of body weight (about 23 g/kg body weight). This feeding was similarly provided once daily throughout a 28-day test period. Fresh tap water was freely available to all animals throughout the studies.

At the conclusion of the test period, the cats were anesthetized and buccal (cheek) surfaces of their posterior teeth were clinically examined for the presence of calculus using the method developed by Schiff as further modified and validated by Logan and Boyce (Vet. Dent. 11(2):58–63, 1994). For this examination, the buccal surface of each tooth is divided vertically into thirds and each third is assigned a numerical score of 0 to 4 based on calculus coverage as follows: 0=none; 1=less than 24% coverage; 2=25 to 49% coverage; 3=50 to 74% coverage; 4=greater than 75% coverage. The individual tooth surface score is the sum of the 3 tooth surfaces. A mean tooth surface score for each cat was obtained by summating the individual tooth surface scores and dividing by the number of teeth graded.

The method used to determine the presence of calculus formation in the dogs was slightly different than the one used for the cats. At the conclusion of the test period, the dogs were anesthetized and buccal (cheek) surfaces of their posterior teeth were clinically examined for the presence of calculus using a grading system similar to the Volpe-Manhold index used in human clinical trials of anticalculus agents. For this examination, each tooth surface was assigned a numerical score of 0 to 4 based on the amount of tooth surface covered with calculus as follows: 0=none; 1=less than 10% coverage; 2=10 to 33% coverage; 3=between 33 and 66% coverage; 4=greater than 66% coverage. The individual tooth surface scores were summated and then divided by the number of tooth surfaces graded to obtain a mean tooth surface score for each dog.

The calculus scores obtained during the baseline/pre-test period were considered to reflect the normal rate of calculus formation for each animal and were used to stratify the animals into groups for all subsequent tests. For example, for a planned 4-group test, the individual animal scores were ranked from the highest to lowest, stratified into blocks of 4 (i.e., the 4 highest scores comprised the first block, the next 4 highest scores comprised the second block, etc.), and then randomly assigned within blocks to each of the 4 groups (so-called randomized block procedure). Thus, each group was comprised of randomly-selected representative animals from each block.

In all experimental studies, the clinical examinations were performed without knowledge of treatment groups by an examiner not otherwise involved in group assignment or daily feeding regimens. Further, the sequence of examinations was randomized to minimize systematic bias due to examiner fatigue, etc.

For each experiment, the animals were given a thorough dental prophylaxis immediately prior to initiation of the study. The animals were divided into the desired number of groups using the previously-described randomized block assignment procedure. The designated feeding regimens were provided beginning with the evening feeding following the prophylaxis, for 4 consecutive weeks. Food consumption was monitored for each animal at each feeding to assure that experimental differences were not confounded by differences in food consumption. At the end of the 28-day test period, the animals were anesthetized and examined for dental calculus formation as previously described. The data were subsequently analyzed using conventional biostatistical procedures, which routinely involved an analysis of variance (ANOVA) with the Newman-Keuls test procedure used to identify statistically significant (p is less that 0.05) intergroup differences. Between experiments the cats were maintained on a commercially-available Kal Kan Crave® dry brand cat food regimen for a one-week (minimum) "washout" period to eliminate any possible carryover effects from the previous test and the dogs were maintained on a commercially-available Waltham Dry Adult Conditioning Formula® brand dog food regimen for the same amount of time, for the same purpose.

EXAMPLE 1

An initial study was conducted to determine the efficacy of three different organic polycarboxylic acid sequestering agents in reducing calculus formation in cats. For this study, the sequestering agents were applied as a coating to the surface of dry, nutritionally-complete cat food that previously had been coated with 0.5 weight-% phosphoric acid. The cat food was then quickly dried in an oven. After drying, chemical analysis was performed on the cat food to determine the final concentration (wt/wt) of sequestering agent in the coated food. The placebo diet was coated with a non-acid-containing aqueous solution in a fashion similar to the test cat food and then dried. The results of the study are summarized in the following table.

TABLE 1

Effect of Different Polycarboxylic Acid Sequestering
Agent Coatings Upon Calculus Formation in Cats

| Agent Tested | Number of Cats | Calculus Score | Percent Reduction |
|---|---|---|---|
| None | 6 | 1.19 + −0.29** | — |
| Citric Acid (0.6% wt/wt) | 6 | 0.89 + −0.17 | 25 |
| Fumaric Acid (0.6% wt/wt) | 6 | 0.69 + −0.31 | 42 |
| Malic Acid (0.6% wt/wt) | 6 | 0.39 + −0.13 | 67 |

**Standard error of the mean

The results of this study indicate that all of the polycarboxylic acid sequestering agents tested resulted in a decrease in calculus formation in the cats. Additionally, the data from this study indicate that the use of malic acid as a coating was appreciably more effective than either citric acid or fumaric acid.

EXAMPLE 2

A study was conducted in order to confirm the effect of polycarboxylic acid sequestering agents upon calculus formation in cats.

In this study, 2.0 ml of a 3.0% (wt/vol) solution of each polycarboxylic acid sequestering agent was applied once daily directly to the teeth of the test animal, using a syringe. Due to taste and cost considerations, the polycarboxylic acid sequestering agents employed in this test were citric acid and malic acid. The placebo solution, water, was applied daily to the teeth of each cat in a similar fashion as the solutions listed above. The results of this study are summarized in the following table.

TABLE 2

Effect of Solutions of Polycarboxylic Acid Sequestering
Agents Upon Calculus Formation in Cats

| Agent Tested | Number of Cats | Calculus Score | Percent Reduction |
|---|---|---|---|
| Water | 7 | 2.84 + −0.59** | — |
| Citric Acid (3.0%) | 7 | 1.96 + −0.48 | 31 |
| Malic Acid (3.0%) | 7 | 1.86 + −0.23 | 35 |

**Standard error of the mean

Both citric acid and malic acid resulted in modest reductions in calculus formation when they were applied directly to the teeth of the cats at an elevated concentration of 3.0%. Compared with the results shown in Example 1, the results of this study support the hypothesis that placing the sequestering agents on dry food as a surface coating results in a greater calculus-reducing efficacy due to the periodic exposure of the dental plaque to the agent several times during a 24-hour period, as cats generally eat small amounts of food at periodic intervals throughout each 24-hour period. A comparison of the results of these two studies also suggest that malic acid may be more readily released from the surface coating of the food than citric acid.

EXAMPLE 3

An additional study was conducted to compare different concentrations of malic acid as coatings on a dry diet for cats. For this study, the sequestering agent, malic acid, was applied as a coating to the surface of dry, nutritionally-complete cat food that previously had been coated with 0.5 weight-% phosphoric acid. The cat food was then quickly dried in an oven. After drying, chemical analysis was performed on the cat food to determine the final concentration (wt/wt) of sequestering agent in the coated food. The placebo diet was coated with a non-acid-containing aqueous solution in a fashion similar to the test cat food and then dried. The results are summarized in Table 3.

TABLE 3

Effect of Different Malic Acid Coatings on
Calculus Formation in Cats

| Agent Tested | Number of Cats | Calculus Score | Percent Reduction |
|---|---|---|---|
| Malic Acid (1.8% wt/wt) | 6 | 1.69 + −0.40** | (−4%) |
| None | 6 | 1.63 + −0.57 | — |
| Malic Acid (0.6% wt/wt) | 6 | 1.44 + −0.51 | 12% |
| Malic Acid (1.2% wt/wt) | 6 | 1.01 + −0.06 | 38% |

**Standard error of the mean

The data from Example 3 indicate that the use of malic acid at a concentration of 1.2% resulted in a 38% reduction in calculus formation in the cats, while a very modest effect was observed with a concentration of 0.6% and no reduction was observed with an elevated concentration of 1.8% as a coating. The latter observation appeared to be due to the adverse effect of higher concentrations on the palatability of the food.

EXAMPLE 4

A study was conducted using dogs to assess the efficacy of two polycarboxylic acid sequestering agents, citric acid and malic acid, upon calculus formation in dogs. As in the previous study in cats (Example 2), a 3.0% (wt/vol) solution of each polycarboxylic acid sequestering agent was made and applied topically via syringe to the posterior teeth of the dogs once daily throughout the 28-day experimental period. The results are summarized in Table 4.

TABLE 4

Effect of Solutions of Polycarboxylic Acid Sequestering Agents on Calculus Formation in Dogs

| Agent Tested | Number of Dogs | Calculus Score | Percent Reduction |
| --- | --- | --- | --- |
| Water | 8 | 1.95 + −0.38** | — |
| Citric Acid (3% wt/vol) | 8 | 1.90 + −0.27 | 3 |
| Malic Acid (3% wt/vol) | 8 | 1.33 + −0.24 | 32 |

**Standard error of the mean

The results of this study confirm the efficacy of malic acid to prevent dental calculus formation in dogs.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of inhibiting dental calculus on the teeth of a dental calculus forming animal comprising feeding said animal a dry pet food product comprising an acidulent amount of phosphoric acid, wherein said food product further comprises an amount of malic acid sequestering agent effective to prevent, inhibit, or reduce the rate of formation of dental calculus deposits, wherein said malic acid is coated onto the surface of the food product so that it contacts the teeth of said animal upon feeding, and wherein said food product does not contain sodium hexametaphosphate.

2. The method of claim 1 wherein said effective concentration of malic acid is about 0.25–2.0% by weight of the food product.

3. The method of claim 1 wherein said animal is a mammal.

4. The method of claim 3 wherein said mammal is a dog or cat.

5. The method of claim 1 wherein said food product is a dog ration or a cat ration.

6. The method of claim 1 wherein said food product is a dog snack food or a cat snack food.

7. A dry pet food product which inhibits dental calculus on the teeth of dental calculus forming animals upon feeding to said animals, wherein said food product consists essentially of an acidulent amount of phosphoric acid, and wherein said food product further comprises malic acid in an amount effective to prevent, inhibit, or reduce the rate of formation of dental calculus deposits, wherein said malic acid is coated onto the surface of the food product so that it contacts the teeth of said animal upon said feeding, and wherein said food product does not contain sodium hexametaphosphate.

8. The food product of claim 7 wherein said effective concentration of malic acid is about 0.25–2.0% by weight of the food product.

9. The food product of claim 7 wherein said animal is a mammal.

10. The food product of claim 9 wherein said mammal is a cat or dog.

11. The food product of claim 7 which is a dog ration or a cat ration.

12. The food product of claim 7 which is a dog snack food or a cat snack food.

13. The method of claim 1 wherein said animal is a domesticated animal.

14. The food product of claim 7 wherein said animal is a domesticated animal.

* * * * *

UNITED STATES PATENT AND TRADEMARK OFFICE
Certificate

Patent No. 6,080,419                                                                               Patented: June 27, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: George K. Stookey, Noblesville, IN; Tiffany Bierer, Fullerton, CA; and Graeme Blackwood, Dana Point, CA.

Signed and Sealed this Fifth Day of October 2004.

FREDERICK F. KRASS
*Supervisory Patent Examiner*
Art Unit 1614